United States Patent
Zubler

(10) Patent No.: US 8,777,610 B2
(45) Date of Patent: Jul. 15, 2014

(54) METHOD FOR HEATING A PRE-WARMED MUFFLE USED FOR DENTAL CERAMICS IN A DENTAL FURNACE AND CONTROL DEVICE AND FURNACE CONTAINING SAID DEVICE

(75) Inventor: Kurt Zubler, Neu-Ulm (DE)

(73) Assignee: Zubler Geratebau GmbH, Ulm-Jungingen (DE)

( * ) Notice: Subject to any disclaimer, the term of this patent is extended or adjusted under 35 U.S.C. 154(b) by 1476 days.

(21) Appl. No.: 12/376,087

(22) PCT Filed: Aug. 1, 2007

(86) PCT No.: PCT/EP2007/006800
§ 371 (c)(1),
(2), (4) Date: Mar. 4, 2011

(87) PCT Pub. No.: WO2008/014989
PCT Pub. Date: Feb. 7, 2008

(65) Prior Publication Data
US 2011/0147968 A1 Jun. 23, 2011

(30) Foreign Application Priority Data
Aug. 1, 2006 (DE) .......................... 10 2006 036 132

(51) Int. Cl.
*F27B 5/04* (2006.01)
(52) U.S. Cl.
USPC .......................................... 432/205; 219/390
(58) Field of Classification Search
USPC ............. 432/18, 51, 205, 241, 247, 249, 253; 219/390, 392, 407, 521, 530; 433/215
See application file for complete search history.

(56) References Cited

U.S. PATENT DOCUMENTS

| | | | | |
|---|---|---|---|---|
| 5,702,514 A | * | 12/1997 | Petticrew | 106/35 |
| 6,303,059 B1 | | 10/2001 | Foser et al. | |
| 7,325,433 B2 | * | 2/2008 | Foser | 72/342.8 |
| 7,925,374 B2 | * | 4/2011 | Andersson et al. | 700/206 |
| 2005/0204796 A1 | * | 9/2005 | Foser | 72/342.8 |
| 2013/0153561 A1 | * | 6/2013 | Jussel | 219/390 |

FOREIGN PATENT DOCUMENTS

| | | |
|---|---|---|
| DE | 1926875 | 4/1970 |
| DE | 3732041 | 4/1989 |
| DE | 3831539 | 3/1990 |
| WO | WO2005116557 | 12/2005 |

* cited by examiner

*Primary Examiner* — Gregory A Wilson
(74) *Attorney, Agent, or Firm* — Myers Andras LLP; Joseph C. Andras

(57) ABSTRACT

For a simplified method for heating a pre-warmed muffle used for dental ceramics in a dental furnace, wherein a saving of time in heating before the pressing and also a parallel heating of the muffles should be made possible, the following steps are suggested: a) heating of the muffle to a maximal temperature ($T_{max}$), which is above the pressing temperature ($T_{press}$), in which pressing is carried out, b) possibly keeping the muffle at a maximal temperature ($T_{max}$) during a first pause ($t_{-1}$), c) cooling of the muffle to a minimal temperature ($T_{min}$), which is at most as high as the pressing temperature ($T_{press}$), and d) keeping the muffle at a minimal temperature ($T_{min}$) during a second pause (t2). In addition, a corresponding control device for the dental furnace and a furnace equipped with this kind of control device are produced.

15 Claims, 2 Drawing Sheets

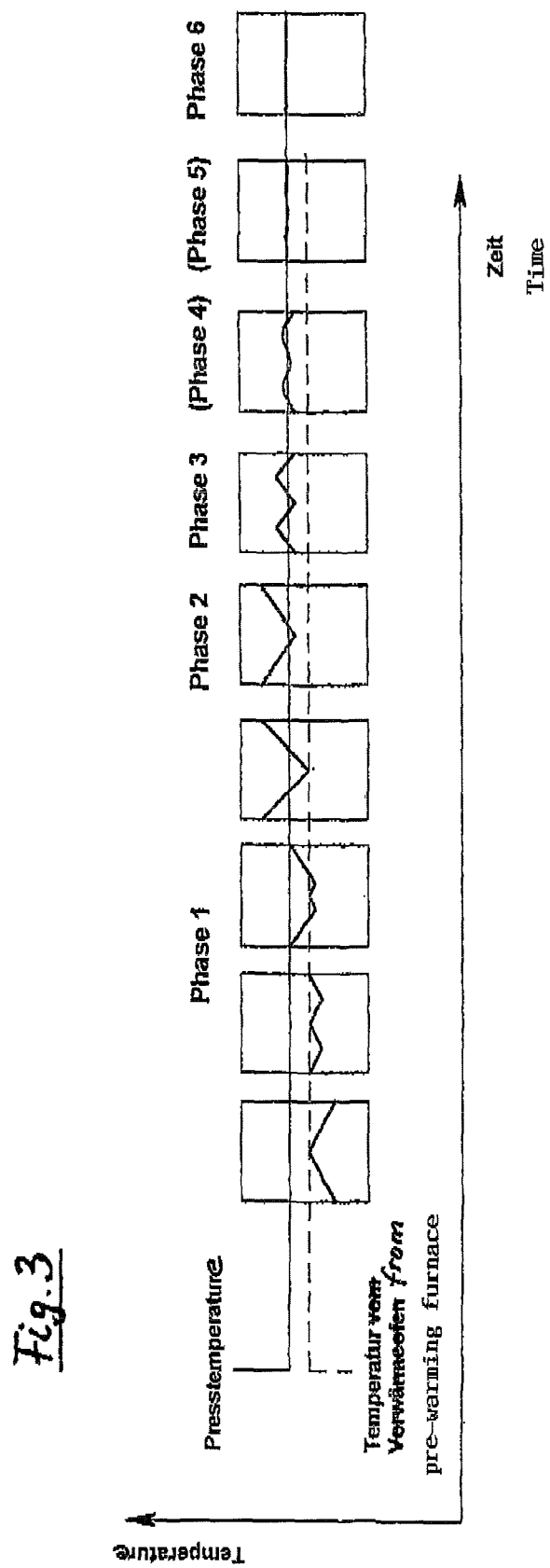

METHOD FOR HEATING A PRE-WARMED MUFFLE USED FOR DENTAL CERAMICS IN A DENTAL FURNACE AND CONTROL DEVICE AND FURNACE CONTAINING SAID DEVICE

BACKGROUND OF THE INVENTION (1) Field of the Invention

The invention relates to a method for heating of a pre-warmed press muffle used for dental ceramics in a press furnace, as well as a control device and a furnace, which includes such a control device.

(2) Description of Related Art

So far it was assumed that input of a target temperature, a heating rate and a relative long holding time on the target temperature sufficiently defines the method for heating of a press muffle used for dental ceramics, before the pressing operation, as part of a press program starts. The input temperature is held constant and coincides more or less accurately with the actual temperature in the press muffle (also shortly named "muffle" in the following), depending on the type of furnace. This method is schematically shown in FIG. 2. The process specifications of the ceramics manufacturers warn of over-heating and refer to the coincidence of the prescribed temperatures in the process. Consequently, as specified above, the only usual method since many years is to control the press furnaces by adjusting the target temperature as maximum temperature and to heat-up the entire muffle slowly to this temperature. Since embedding masses, forming the muffles exhibit a very low thermal conductivity, long heating times are required. Nevertheless, the actual temperature inside the muffle is still up to 30° C. below the adjusted target temperature on beginning of the pressing operation. The indication of the processing temperature of the ceramic is usually adapted to this problem and has a higher value than actually required. Tests and measurements within the muffles evidenced this.

When defective pressing (the form is incompletely filled) happens, it is often attempted to extend the holding time or to correct the target temperature to a higher level. However, both measures change nothing in the fact that a temperature gradient exists within the muffles from the outside to the inside (e.g. up to 60° C. in a muffle having 300 g). Thus, defective pressing by over-heating or early solidification of the ceramic on the path into the form often occurs. Good pre-warming can be achieved with muffles having 100 g embedding mass (diameter 38 mm). However, for more complex works such as multiple models the use of muffle forms for 200 g embedding mass (diameter 48 mm) is required. Even larger works (e.g. multi-element dental bridges) were so far excluded of the technology of the ceramics pressing. On the one hand, this is to the missing indication of existing ceramic materials (large bridge constructions require a high breaking strength), on the other hand because of the problem to heat the required muffles with 300 g (diameter 62 mm) in a homogeneous manner. A new technology (press-to-metal), which is used more frequently, eliminates the problem of flexural strength of dental ceramics. In this method a frame of a dental metal alloy serves as basis for the press ceramics. While this technology is established since more than 50 years in dentistry by applying the ceramic by subsequent layers, the press-to-metal method is substantially more effective to create high-quality artificial dentures. In the future, this method requires uniform heating, in particular of larger press muffles.

Many dental technicians consider ceramics work of high complexity as "not feasible". Hardly a work-piece succeeds without traces of material damages or discolorations. In addition, high cost and urgency oppose the required long program times of the heating phase. Even with small muffles the temperature is often not exact and uniform enough, so that in particular bright dental colours become greyish. Quality problems often lead to repetition of work or expensive repairs.

BRIEF SUMMARY OF THE INVENTION

The present invention objects to a simplified process for the production of press ceramics in dentistry in order to avoid the disadvantages described above and to save of time for pre-warming before pressing as well as providing simultaneously a uniform heating of muffles, such that an optimum flow of the ceramic and thus fewer defective pressing is achieved as well as avoiding material damages by overheating. Further, a suitable furnace control device for program input at a press furnace as well as a correspondingly equipped furnace for performing this method is provided.

This object is achieved by a method for heating of a press muffle before the pressing operation in a furnace, used for dental ceramics according to claim 1 as well as with a corresponding control device according to claim 9 and a furnace according to claim 11 comprising such a control device. Preferred embodiments of the invention are subject matter of the dependent claims.

The invention is based on the fact that with heating of the environment of a colder object this object does not accept the ambient temperature immediately. Heat capacity and thermal conductivity characterise the inertial behaviour of bodies on heating. With good insulation and/or full surface heating the body is uniformly warmed up after a certain time. Altogether it lasts very long, when the ambient temperature and/or the heating temperature equals the desired final temperature of the body, in particular if it concerns a material with low thermal conductivity. The temperature equalizing is sloweddown the smaller the temperature difference between final temperature and ambient temperature is. Thus, the approach according to the invention consists in transporting certain amount of heat by a temporal limited increased level of the predetermined temperature in shorter time from the outside into the interior of the muffles. The temperature should arrive at the centre, where the ceramics blanks (pellets) are located. The new method is based on the prior art arrangement of pressing ceramics, with which the ceramic material arrives in the outer regions of the muffle only with the pressing operation at the end of the warming-up phase of the die. Here it is important that the temperature gradient and the temperature level can be higher in the outer regions of the muffle, in which no ceramic material is located, yet, than the press temperature, as long as the pressing operation has not yet started. The pressing operation is initiated only after a cooling phase and a thus introduced temperature equalizing in the muffle. With full ceramics objects there's the option to highly overheat, thus reducing the time of the pressing operation significantly.

According to the invention, the press muffle is heated to a maximum temperature being significantly above the press temperature, i.e. that temperature at which the pressing operation is performed. This serves for introducing heat as much as possible in the initial phase of the heating process into the press muffle, and there is no risk of overheating the ceramics blanks introduced into the press muffle as the introduction of the heat into the interior of the press muffle is only relatively slow due to the low thermal conductivity of the material, of which the press muffle consists. After reaching the maximum temperature the heater of the furnace is switched off, such that the outside of the press muffle cools down, but the heat transport into the still cooler interior of the press muffle is continued, nevertheless. Thus, this phase serves to obtain a temperature distribution within the press muffle to be as uniform as possible. The cooling of the press muffle is made to a minimum temperature, which is in the simplest case the same as press temperature, but can be also lower. The press muffle will then be held on the minimum temperature for a subsequent period, in order to improve the uniformity of the temperature distribution. This heating procedure is well applicable for press muffles with a mass of 100 g. With a mass of the press muffle of 200 g or more, however, it is still required to hold the press muffle at the maximum temperature during a first holding time after reaching this temperature in order to transport the required amount of heat into the press muffle, before it may cool down. According to the invention, the press muffle can thus be heated with a maximum temperature, which is significantly higher than the prescribed processing temperature of the ceramic, preferably between 50° C. and 200° C. or more than the press temperature.

Adapting the maximum temperature to the used weight of the press muffle is preferably made by adding a temperature difference Tm1 to the press temperature for the employed dental ceramics, as follows for common muffle masses and correspondingly interpolated and/or extrapolated, if necessary:

Tm1 (100 g)=180° C.
Tm1 (200 g)=180° C.
Tm1 (300 g)=200° C.

If the maximum temperature, given for an optimum short heating-up time, cannot be reached by the furnace, it is preferred to determine the first holding time in such a way that the difference between the maximum temperature and the furnace limit temperature is multiplied with an experimentally determined factor k, that considers the various muffle sizes. As reference points the most usual three muffle sizes are considered in the following values, which can be extrapolated or interpolated for different muffle sizes, if necessary:

$k_{100g}$=0.05 min/° C.
$k_{200g}$=0.075 min/° C.
$k_{300g}$=0.1 min/° C.

If the maximum temperature is limited due to an object limit temperature, which is given by the objects embedded in the press muffle, as for example the ceramic or a opaquer, the furnace limit temperature is preferably defined by adding a temperature difference Tm2, dependent on the weight of the press muffle, to the object limit temperature, which is approximately determined in an empirical way for the most usual muffle weights as follows and which can be correspondingly interpolated for intermediate muffle weights:

Tm2 (100 g)=0° C.
Tm2 (200 g)=50° C.
Tm2 (300 g)=50° C.

In order to provide a still more uniform temperature distribution within the muffles, it is favourable to cool down the heated press muffle to a temperature of preferably 20° C.-50° C. below the press temperature and to hold this minimum temperature for a holding time of approximate 0.5-4 minutes, preferably for about 1-3 minutes and subsequently to heat-up back to the press temperature, wherein the press muffle is then hold about 1-3 minutes, preferably 1-2 minutes, on this press temperature before the actual pressing operation begins. Of course, the press muffle is also held on the press temperature during the pressing operation.

The invention also provides a control device for a furnace for heating of a press muffle before the actual pressing operation of dental ceramics, wherein automatic performing of the aforementioned methods is possible. For this purpose the respective parameters as temperatures, holding times and the press muffle sizes and preferably also the parameters of the corresponding heating rates and cooling rates have to be input into the control device. Preferably also the amount of dental ceramics and the so called embedding mass factor can be entered, so that the control device can determine an automatic optimum temperature profile for performing the heating process of the press muffle. An additional subject matter of the invention is a ceramics or press furnace including the foregoing control device for performing the pressing operation.

BRIEF DESCRIPTION OF THE SEVERAL VIEWS OF THE DRAWINGS

Other advantages, characteristics and features of the invention result from the subsequent description of preferred, but not limiting embodiments of the invention on the basis the schematic drawings. They show.

DETAILED DESCRIPTION OF THE PREFERRED EMBODIMENTS

Figure 2:
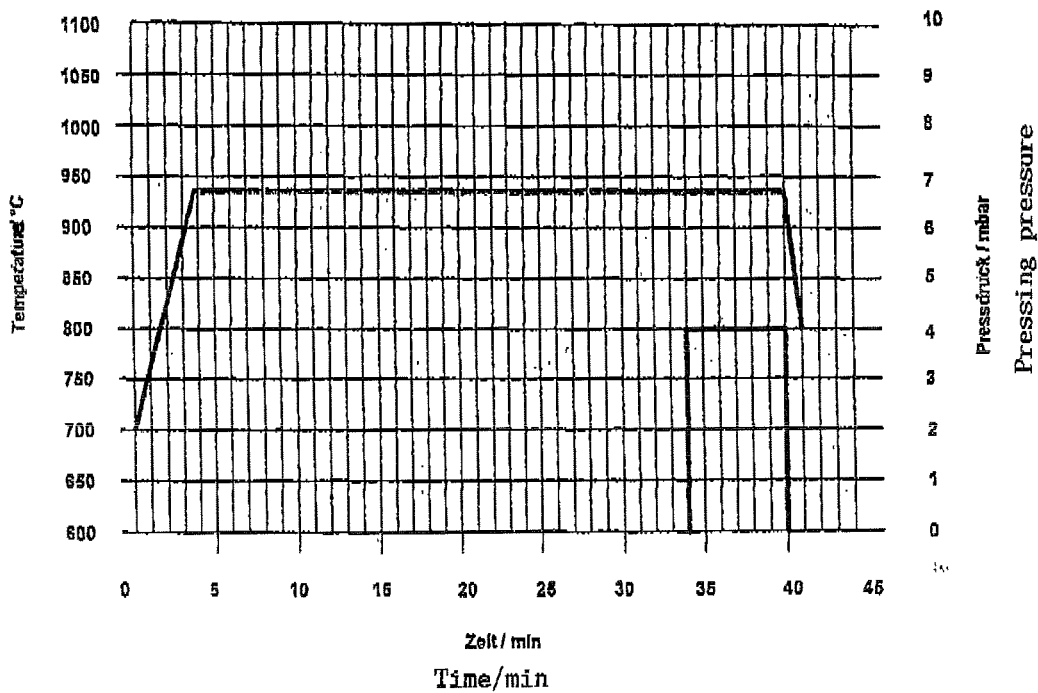
Figure 1:
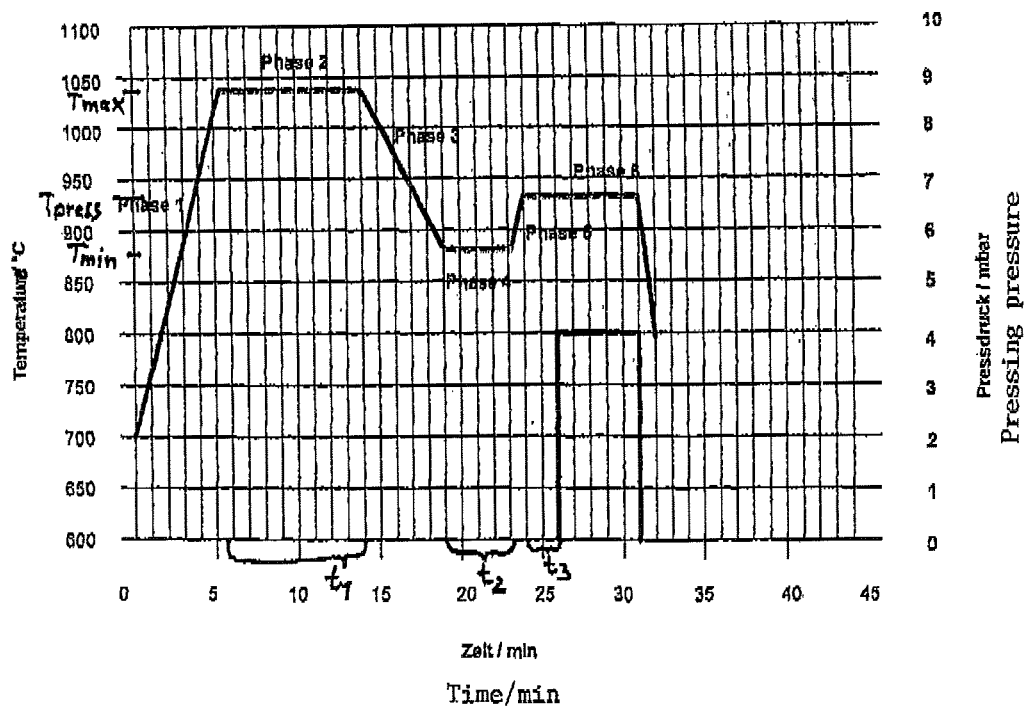
FIG. 1 a schematic representation of the temperature gradient with an embodiment of the invention process, FIG. 2 a schematic representation of the temperature gradient with the conventional method, and FIG. 3 a simplified temperature gradient in the cross section of a muffle, heated by the invention method (actually, the temperature gradient is not linear, but follows a logarithmic function, as the cross-section continuously varies such that heat flow is an integral on the radius).

With reference to FIG. 1 a typical temperature gradient during performing of the invention method is now explained as example in qualitative manner, wherein the corresponding temperature gradients in the cross section of the muffles are shown in the single phases in FIG. 3.

Starting with phase 1, the preheating temperature inside the press muffle is approximately 850° C., resulting from a preheating furnace, wherein the outer zones of the press muffle are cooled down to approximately 700° C. by the transport to the press furnace. Then, the press muffle is heated at the outside to the press temperature Tpress of 940° C. or more, as long as the heating rate Vh of preferably 60° C./min is applied up to the maximum temperature Tmax of 1040° C.

In phase 2 the maximum temperature Tmax is then held during a first holding time t1. This holding time t1 is particularly required with muffle sizes starting from 200 g, since the heating duration is not sufficient alone to provide the required heat amount for reaching the desired temperature in the interior of the muffle. An accurate boundary of the phase 2 to phase 1 cannot be given with respect to FIG. 3, since the heat penetrates to the centre of the press muffle such that the temperature in the press muffle is nearly equal to the press temperature. The outer regions of the press muffle are still substantially hot, namely at the maximum temperature Tmax.

In phase 3 then a cooling of the outer zones of the press muffle occurs, preferably with a cooling rate Vk of 30° C./min, which should take place in principle to an external temperature, which corresponds either to the press temperature Tpress or to slightly lower temperature, the latter being referred to as minimum temperature Tmin. In the represented example the minimum temperature Tmin is about 880° C. Cooling-down to the minimum temperature Tmin is then preferred, when a particularly exact warming of the outer regions of the muffle is to be achieved.

In phase 4, a second holding time t2 of approximately 4 min—which can amount to only about half a minute at correspondingly high minimum temperature Tmin, as well—causes a temperature equalizing within the muffle. The minimum temperature Tmin is held for a short time until the conditions for an optimum temperature equalizing are achieved.

In phase 5, further heating of the outer regions results in a press temperature Tpress of 940° C.—again with the heating rate Vh of preferably 60° C./min—accompanied by further temperature equalizing within the press muffle.

After that relatively short heating duration of phase 5 the press temperature is still held in phase 6 during a third holding time t3 of approximately 1 to 3 min, up to triggering of the pressing operation. The press temperature is then held, until the pressing operation is completed. In this phase the temperature gradient within the muffle is almost homogeneous and thus ideal for an optimum pressing operation.

The aforementioned phases 4 and 5 support above all the achievement of a perfect uniform heating up. Quite good results can also be achieved depending upon the circumstances, if phase 3 cools down only to press temperature Tpress and a holding time is waited for e.g. 3 min, before the pressing operation is triggered.

In the following it will be explained, how the maximum temperature of the furnace, the size of the heated muffles and the limit temperatures of embedded objects in the edge regions of the muffles, f. i. frames and opaque layering, influence the respective temperature and time parameter in accordance with the present invention.

The fastest possibility for the heat input is basically a heating to a Tmax as high as possible and a subsequent cooling without holding time, i.e. t1=0. If the maximum temperature Tmax would not be limited, it can be defined depending on the muffle size as follows:

$$T\text{max} = T\text{press} + Tm1,$$

wherein the press temperature Tpress is 860° C. to 980° C.

Tm1 is a constant temperature difference, which is determined for the three various muffle sizes of 100 g, 200 g and 300 g as follows:
Tm1 (100 g)=160° C.
Tm1 (200 g)=180° C.
Tm1 (300 g)=200° C.

Example

A ceramic material for 900° C. press temperature is to be pressed in a muffle of 200 g. Then follows:

$$T\text{max} = 900° C. + 180° C. = 1080° C.$$

If the maximum temperature Tmax is limited by the performance of the press furnace, the first holding time t1 should be introduced, in particular at higher press temperatures and large muffles, since the energy is not sufficient for warming-up the muffles otherwise, when the limited maximum temperature Tmax is changed over immediately to the cooling phase. The predetermined limited maximum temperature is subsequently cited as Tlimit. The maximum temperature Tmax is then only a theoretical value, and the actual furnace temperature is Tlimit. With linear approximation the subsequent equation applies to the first holding time t1

$$t1 = (T\text{max} - T\text{limit})*k = (T\text{press} + Tm1 - T\text{limit})*k$$

with same Tpress as above and Tmax>Tlimit.

k is a factor, which is experimentally determined for the three various muffle sizes of 100 g, 200 g and 300 g as follows:

$k_{100g}$=0.05 min/° C.
$k_{200g}$=0.075 min/° C.
$k_{300g}$=0.1 min/° C.

Example

A ceramic material for 940° C. press temperature is to be pressed in a muffle of 300 g, and the adjustable maximum temperature of the press furnace amounts to 1100° C. Then follows:

$$t1 = (940° C. + 200° C. - 1100° C.)*0.1 \text{ min}/° C. = 40° C.*0.1 \text{ min}/° C. = 4 \text{ min}.$$

If the maximum temperature Tmax is limited by embedded objects, the safest variant is of course to use this limit temperature Tobjekt as Tlimit without further increase and to employ it for calculation of the holding time t1 in the formula. However, the entire press time will be extended so that a temporal advantage is limited in relation to the conventional melting method. But it is convenient to use a limited temperature increase Tm2 in favour of an optimum heating. The subsequent equation results:

$$T\text{limit} = T\text{objekt} + Tm2$$

The temperature Tobjekt may not be exceeded in the range of the muffles, where the embedded objects are positioned. According to temperature measurements in these ranges at least the subsequent increase Tm2 is possible:
Tm2 (100 g)=0° C.
Tm2 (200 g) al 50° C.
Tm2 (300 g)=50° C.

With the muffle of 100 g the outside and average temperatures coincide with the furnace temperature; only in the centre (full ceramics) temperature increase is applicable. With the muffles of 200 g or of 300 g distinguishing is not required, since different warming rates are already considered by the factor k. Further, only slight temperature differences arise relative to the muffle diameter in slight distance of the outer edge of the muffles, where embedded objects can be located.

Example

A metal frame is to be over-pressed with ceramic for 920° C. in a muffle of 200 g. The opaque layer on the metal frame is only stable up to 950° C.
Tpress=920° C.
Tobjekt=950° C.
Tm1 (200 g)=180° C.
Tm2 (200 g)=50° C.
Tpress=920° C.
$k_{200g}$=0.075 min/° C.

$$t1 = \{(T\text{Press} + Tm1) - (T\text{objekt} + Tm2)\}*k = (1100° C. - 1000° C.)*k = 100*k$$

$$t1 = 7.5 \text{ min}, T\text{limit} = 1000° C.$$

The press-on-metal method does not exceed the processing temperature of the opaquer, although the embedded frame can also be in edge regions of the muffle. The distance to the press temperature is sufficient to realize a uniform warming-up of a large muffle.

The accurate embodiment of the control device according to the invention for automatic performing of the aforementioned methods as well as the furnace according to the invention equipped with it is not explained in detailed explanation, since the realization will not pose any problem to the skilled technician in view of the teaching of the invention method.

To sum up, it should be noted that the present invention enables a uniform warming-up of muffles of all sizes. Thus, perfect quality and time saving as well as pressing of complex, multi-element bridges and new techniques are possible, e.g. zircon, metal, alumina frames up to 14 members can be over-pressed with ceramics, resulting in new applications. Further, significant reduction of defective pressing and optimum material-sensitive processing of the ceramics is provided in all ranges of the muffles. By a sufficient energy transfer to melt larger ceramic quantities and by homogeneous temperature distribution in the muffles a perfect flow becomes possible. In some cases the decrease of conventional press temperatures is possible. There's no risk that the ceramic becomes greyish, what is particularly important with bright dental colours important, in order to comply with aesthetic claims of the patients.

It is to be noted that the features of the invention described with reference to single embodiments, like certain temperature values and/or ranges or presence of certain phases, can also be present with other embodiments.

The invention claimed is:

1. Method for heating of a pre-warmed press muffle used for dental ceramics in a press furnace, comprising the subsequent steps:
   a) heating the press muffle to a maximum temperature (Tmax), which is above the press temperature (Tpress), at which a pressing operation is performed,
   b) holding the press muffle on the maximum temperature (Tmax) during a first holding time (t1),
   c) cooling of the press muffle to a minimum temperature (Tmin), which is at most as high as the press temperature (Tpress), and
   d) holding of the press muffle on the minimum temperature (Tmin) during a second holding time (t2).

2. Method according to claim 1, characterised in that the maximum temperature (Tmax) is defined by the press temperature (Tpress) plus a temperature difference Tm1 dependent on the mass of the press muffle, wherein Tm1 for various masses of press muffles is approximately:
   Tm1 (100 g)=160° C.
   Tm1 (200 g)=180° C.
   Tm1 (300 g)=200° C.
   and these values may be interpolated and/or extrapolated for different masses of press muffles.

3. Method according to claim 1, characterised in that with limitation of the maximum temperature (Tmax) to furnace limit temperature $T_{limit}$ conditioned by the furnace, the first holding time (t1) is defined by multiplication of the difference between the maximum temperature (Tmax) and the furnace limit temperature $T_{limit}$ with a factor k dependent on the mass of the used press muffle, being approximately:
   $k_{100g}$=0.05 min/° C.
   $k_{200g}$=0.075 min/° C.
   $k_{300g}$=0.1 min/° C.
   and these values may be interpolated and/or extrapolated for different masses of press muffles.

4. Method according to claim 3, characterised in that with limitation of the maximum temperature (Tmax) due to an object limit temperature $T_{objekt}$, which is conditioned by objects embedded into the press muffle, the furnace limit temperature $T_{limit}$ is defined by the object limit temperature $T_{objekt}$ plus a temperature difference Tm2 dependent on the mass of the press muffle, wherein Tm2 for various masses of press muffles is approximately:
   Tm2 (100 g)=0° C.
   Tm2 (200 g)=50° C.
   Tm2 (300 g)=50° C.
   and these values may be interpolated for different masses of press muffles.

5. Method according to claim 1, characterised in that the minimum temperature (Tmin) is lower than the press temperature (Tpress) and step d) is followed by subsequent steps:
   e) heating-up the press muffle to the press temperature (Tpress) and
   f) holding the press muffle on the press temperature (Tpress) during a third holding time (T3) before the pressing operation.

6. Method according to claim 5, characterised in that the difference between the press temperature (Tpress) and the minimum temperature (Tmin) amounts to about 20 to 50° C.

7. Method according to claim 6, characterised in that the second holding time (t2) amounts to about 0.5 to 4 minutes, preferably about 1 to 3 minutes.

8. Method according to one of claim 6, characterised in that the third holding time (t3) amounts to about 1 to 3 minutes, preferably about 1 to 2 minutes.

9. Method according to claim 5, characterised in that the second holding time (t2) amounts to about 0.5 to 4 minutes, preferably about 1 to 3 minutes.

10. Method according to one of claim 9, characterised in that the third holding time (t3) amounts to about 1 to 3 minutes, preferably about 1 to 2 minutes.

11. Method according to one of claim 5, characterised in that the third holding time (t3) amounts to about 1 to 3 minutes, preferably about 1 to 2 minutes.

12. Control device for a furnace for heating of a press muffle used for dental ceramics before the pressing operation, characterised by an apparatus for the input of the respective temperature, holding times, press muffle parameters and preferably also of the heating rate parameter for performing of a method in accordance with claim 1 and an apparatus for automatic performing of the corresponding method.

13. Control device according to claim 12, characterised by an apparatus for the input of the amount of dental ceramics and the embedding mass factor and an apparatus for the automatic determination of an optimum temperature profile for performing of the corresponding method.

14. Furnace for heating of a press muffle used for dental ceramics before the pressing operation and for performing the pressing operation, characterised by a control device in accordance with claim 13.

15. Furnace for heating of a press muffle used for dental ceramics before the pressing operation and for performing the pressing operation, characterised by a control device in accordance with claim 12.

* * * * *